US010636555B2

(12) United States Patent
Zareei et al.

(10) Patent No.: US 10,636,555 B2
(45) Date of Patent: Apr. 28, 2020

(54) ARTICULATED VIDEO PROBE WITH MAGNETIC STIMULATION

(71) Applicants: Seyed Mostafa Zareei, Isfahan (IR);
Mahdi Barekatain Fard, Isfahan (IR);
Mohammad Hossein Kalbasi Ashtari,
Isfahan (IR)

(72) Inventors: Seyed Mostafa Zareei, Isfahan (IR);
Mahdi Barekatain Fard, Isfahan (IR);
Mohammad Hossein Kalbasi Ashtari,
Isfahan (IR)

(*) Notice: Subject to any disclaimer, the term of this patent is extended or adjusted under 35 U.S.C. 154(b) by 266 days.

(21) Appl. No.: 15/660,702

(22) Filed: Jul. 26, 2017

(65) Prior Publication Data

US 2017/0330665 A1    Nov. 16, 2017

Related U.S. Application Data

(60) Provisional application No. 62/377,808, filed on Aug. 22, 2016.

(51) Int. Cl.

| | | |
|---|---|---|
| H01F 7/06 | (2006.01) |
| B25J 18/06 | (2006.01) |
| B25J 9/12 | (2006.01) |
| B25J 13/06 | (2006.01) |
| B25J 9/06 | (2006.01) |
| A61B 1/008 | (2006.01) |
| A61B 1/005 | (2006.01) |
| A61B 1/00 | (2006.01) |
| H04N 5/225 | (2006.01) |

(52) U.S. Cl.
CPC .......... *H01F 7/064* (2013.01); *A61B 1/008* (2013.01); *A61B 1/0055* (2013.01); *A61B 1/0057* (2013.01); *A61B 1/00158* (2013.01);
*B25J 9/06* (2013.01); *B25J 9/12* (2013.01);
*B25J 13/065* (2013.01); *B25J 18/06* (2013.01); *H04N 5/2253* (2013.01); *H04N 2005/2255* (2013.01)

(58) Field of Classification Search
USPC ......................................... 361/139, 143–144
See application file for complete search history.

(56) References Cited

U.S. PATENT DOCUMENTS

| | | | |
|---|---|---|---|
| 4,790,624 | A | 12/1988 | Van Hoye et al. |
| 5,413,107 | A | 5/1995 | Oakley et al. |
| 5,634,466 | A | 6/1997 | Gruner |
| 5,704,898 | A | 1/1998 | Kokish |
| 2012/0116398 | A1 | 5/2012 | Goldfarb et al. |
| 2013/0002895 | A1 | 1/2013 | McClung |

(Continued)

FOREIGN PATENT DOCUMENTS

CN        104116484        10/2014

*Primary Examiner* — Danny Nguyen
(74) *Attorney, Agent, or Firm* — Bajwa IP Law Firm;
Haris Zaheer Bajwa

(57) ABSTRACT

A video probe is disclosed herein that includes an elongated probe including an articulating portion, and a controller functionally coupled with the elongated probe. The articulating portion may include at least two interconnected links and each link may include opposing electromagnetic coils disposed within the link. The controller may be configured to stimulate the opposing electromagnetic coils to attract/repulse corresponding opposing electromagnetic coils of an adjoining link thereby causing the link to pivot about the axis of the single-axis joint.

6 Claims, 10 Drawing Sheets

(56) References Cited

U.S. PATENT DOCUMENTS

2014/0088356 A1* 3/2014 Matsuo ............... A61B 1/0056
  600/109
2014/0371764 A1* 12/2014 Oyola .................... B25J 18/06
  606/130

* cited by examiner

ARTICULATED VIDEO PROBE WITH MAGNETIC STIMULATION

CROSS REFERENCE TO RELATED APPLICATION

This application claims the benefit of priority from U.S. Provisional Patent Application Ser. No. 62/377,808, filed on Aug. 22, 2016, and entitled "ARTICULATED VIDEO PROBE MECHANISM WITH MAGNETIC STIMULATION," which is incorporated herein by reference in its entirety.

TECHNICAL FIELD

The present disclosure generally relates to probes for capturing and transmitting images, and particularly to an articulated video probe mechanism with magnetic stimulation.

BACKGROUND

A video probe can be used to capture images inside an area of interest. The video probe can include a camera attached to a distal end of an arm, and the arm can be used for navigating the camera inside the area of interest. The arm can be articulated and capable of bending and/or rotating in order to facilitate camera movements within the area of interest, which in most applications is an area with limited access, for example, in medical contexts.

The diameter of most video probes is not more than a few millimeters to allow for running the video probe through small and twisted passages. Most video probes have mechanical controlling systems, such as cable control systems for controlling the arm movements.

Cable control systems must transmit movement commands of a user to the probe via cables. These cables occupy space inside the arm of the probe; as a result, the arm of the probe has to be designed with larger diameters. In addition, in case of long video probes, the odds of command transmission errors become larger.

There is, therefore, a need in the art for a more flexible and controllable probe mechanism which is capable of moving with more accuracy and precision. There is further a need in the art for a new articulation and stimulation mechanism for a video probe that allows for curving the video probe by bending different portions of the video probe in various directions.

SUMMARY

This summary is intended to provide an overview of the subject matter of exemplary embodiments of the present disclosure, and is not intended to identify essential elements or key elements of the subject matter, nor is it intended to be used to determine the scope of the claimed embodiments. The proper scope of the present disclosure may be ascertained from the claims set forth below in view of the detailed description below and the drawings.

In an exemplary embodiment consistent with the present disclosure, a video probe is disclosed. The video probe may include an elongated probe including an articulating portion, and a controller that may be functionally coupled with the elongated probe. The articulating portion may include at least two interconnected links, where each link may be connected to an adjoining link by a single-axis joint. Each link may pivot relative to the adjoining link about an axis of the single-axis joint. Each link may include a first electromagnetic coil that is disposed within the link at a first side thereof, and a second electromagnetic coil at a second side thereof. The controller may be configured to stimulate the first electromagnetic coil to attract a corresponding first electromagnetic coil of an adjoining link and the second electromagnetic coil to repulse a corresponding second electromagnetic coil of an adjoining link thereby causing the link to pivot about the axis of the single-axis joint.

According to an exemplary embodiment, the controller may be coupled with the first electromagnetic coil of each link via electrical wiring extended from the controller through the elongated probe and coupled with the first electromagnetic coil with a first winding direction. The controller may be configured to send electrical signals to the first electromagnetic coil through the electrical wiring to stimulate the first electromagnetic coil of each link to attract a corresponding first electromagnetic coil of an adjoining link.

According to an exemplary embodiment, the controller may be coupled with the second electromagnetic coil of each link via electrical wiring extended from the controller through the elongated probe and coupled with the second electromagnetic coil with a second winding direction. The first winding direction is opposite the second winding direction. The controller may be configured to send electrical signals to the first electromagnetic coil through the electrical wiring to stimulate the first electromagnetic coil of each link to attract a corresponding first electromagnetic coil of an adjoining link.

In another exemplary embodiment consistent with the present disclosure, a video probe is disclosed. The video probe may include an elongated probe that may include an articulating portion, and the articulating portion may include at least a first articulating segment and a second articulating segment. Each articulating segment may include at least two interconnected links, where each link may be connected to an adjoining link by a single-axis joint. Each link may pivot relative to the adjoining link about an axis of the single-axis joint, and each link may include a first electromagnetic coil disposed within the link at a first side thereof, and a second electromagnetic coil at a second side thereof. Each segment may be joined with an adjoining segment by a relative 180° offset rotation from one articulating segment to the next. The video probe may further include a controller that may be functionally coupled with the elongated probe, and the controller may be configured to magnetically stimulate the interconnected links of the first articulating segment thereby causing the first electromagnetic coil to attract a corresponding first electromagnetic coil of an adjoining link and the second electromagnetic coil to repulse a corresponding second electromagnetic coil of an adjoining link. The controller may further be configured to magnetically stimulate the interconnected links of the second articulating segment thereby causing the first electromagnetic coil to attract a corresponding first electromagnetic coil of an adjoining link and the second electromagnetic coil to repulse a corresponding second electromagnetic coil of an adjoining link.

Other systems, methods, features and advantages of the exemplary embodiments will be, or will become, apparent to one of ordinary skill in the art upon examination of the following figures and the accompanying detailed description. It is intended that all such additional systems, methods, features and advantages be included within this description and this summary, be within the scope of and consistent with exemplary embodiments of the present disclosure, and be protected by the following claims.

BRIEF DESCRIPTION OF THE DRAWINGS

The drawing figures depict one or more embodiments in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings.

Disclosed herein is a video probe apparatus for capturing images from inside small and twisted passages. The video probe apparatus may include a control unit and an elongated probe with an image capturing device attached to its distal end. In order to control an orientation of the image capturing device inside the passage, the elongated probe is designed with an articulating portion. The articulating portion is made up of several interconnected links. Here, in order to cause the articulating portion to rotate in a desirable direction, each link is provided with two electromagnetic coils disposed inside each link at either side thereof. The control unit may send electrical signals to these electromagnetic coils in order to stimulate them into attracting or repulsing one another and based on how these electromagnetic coils are stimulated, the articulating section may rotate as a result of the rotational movement of interconnected links.

Figure 1:
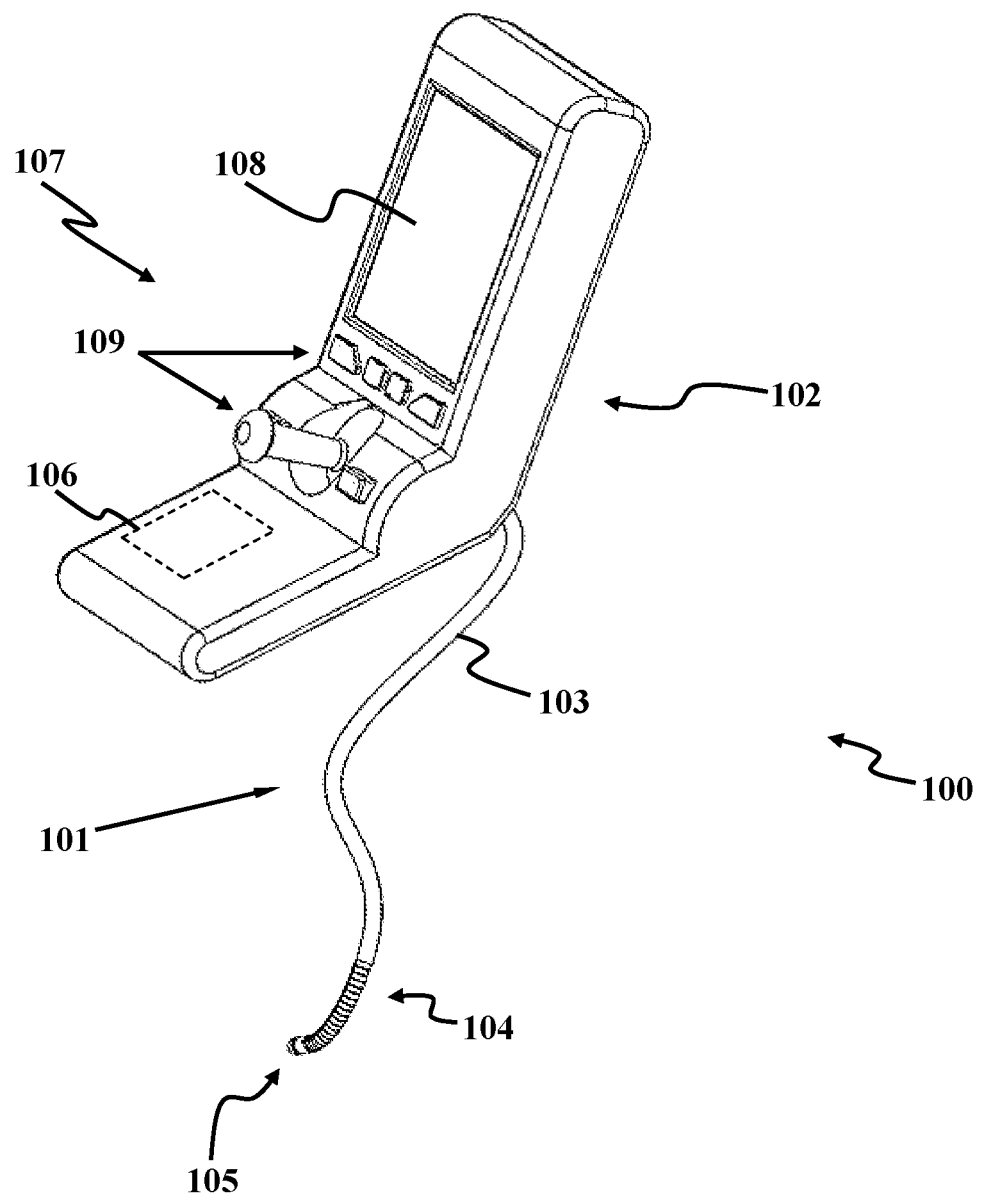
FIG. 1 illustrates a video probe apparatus, consistent with an exemplary embodiment of the present disclosure.

FIG. 1 illustrates a video probe apparatus 100, consistent with an exemplary embodiment of the present disclosure. Video probe apparatus 100 may include an elongated probe 101. A proximal end of elongated probe 101 may be operatively connected to a control system 102. Elongated probe 101 may include a non-articulating portion 103 and an articulating portion 104. A distal end of articulating portion 104 may include, or alternatively may be attached to an image capturing device 105, such as a camera. Control system 102 may be configured to control movements of articulating portion 104 in order to navigate image capturing device 105 along narrow and twisted passages.

Figure 2:
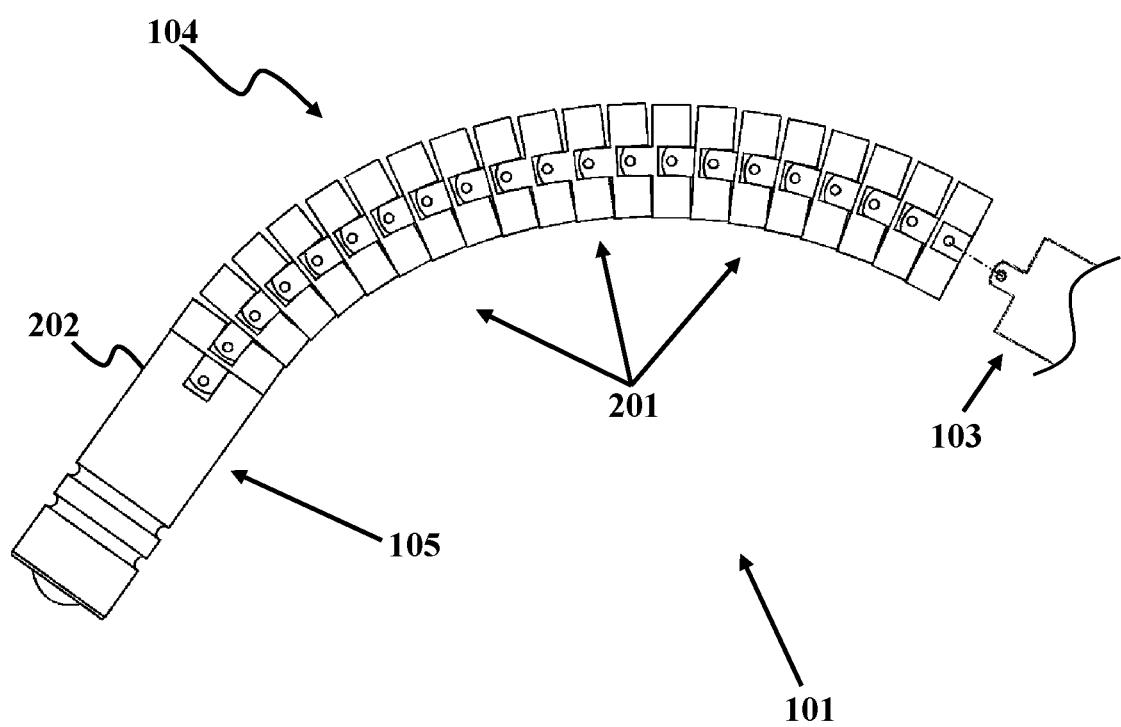
FIG. 2 shows an articulating portion of an elongated probe, consistent with an exemplary embodiment of the present disclosure.

FIG. 2 shows articulating portion 104 of elongated probe 101, consistent with an exemplary embodiment of the present disclosure. Articulating portion 104 may include a number of interconnecting links 201 that form an articulation mechanism, where each link may be joined with an adjoining link via revolute joints and may rotate about a single axis relative to the adjoining link. A proximal end of articulating portion 104 may be coupled with a distal end of non-articulating portion 103 and a distal end of articulating portion 104 may be coupled with image capturing device 105 via for example a cameral link 202.

Figure 3:
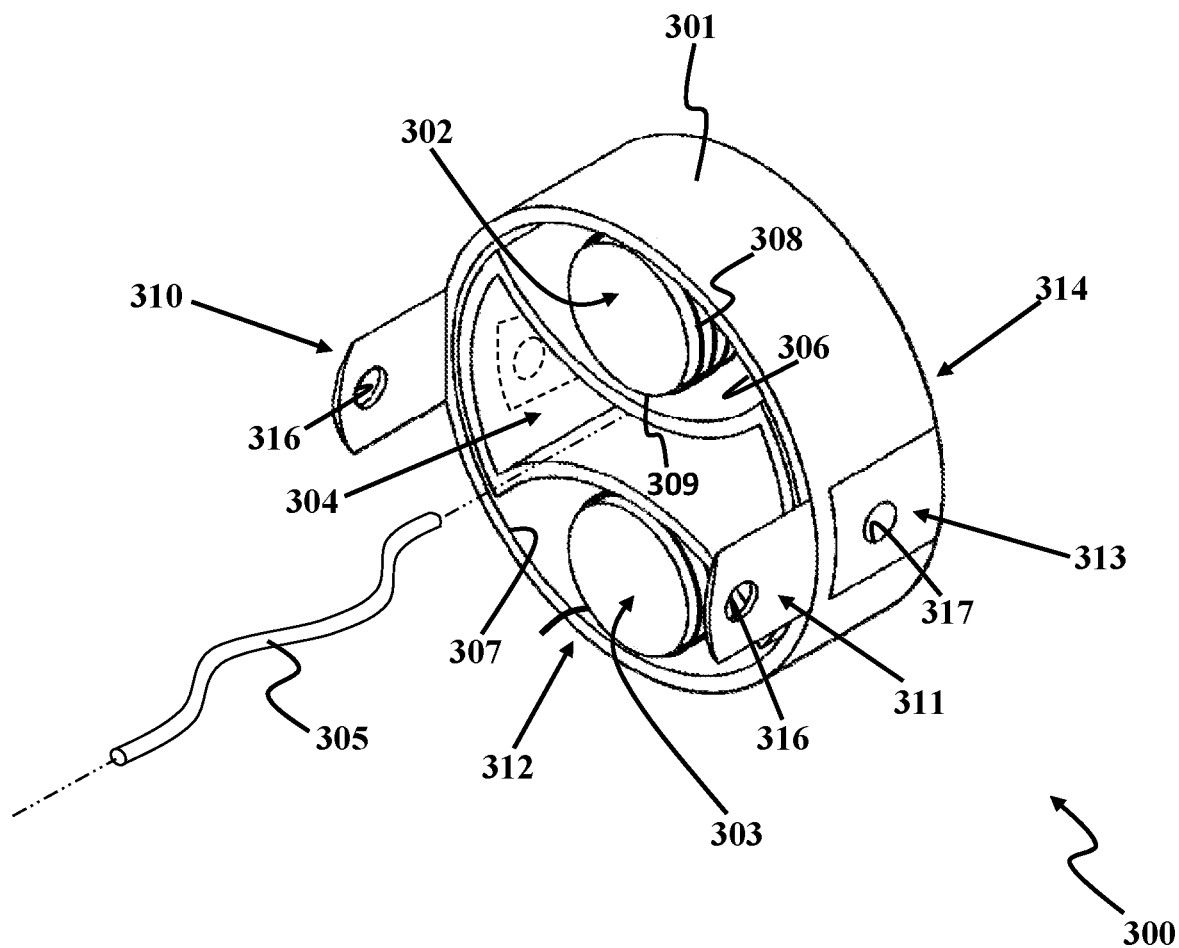
FIG. 3 illustrates a link of an articulating portion of an elongated probe, consistent with an exemplary embodiment of the present disclosure.

FIG. 3 illustrates a link 300 of an articulating portion of an elongated probe, consistent with an exemplary embodiment of the present disclosure. Link 300 may be similar to links 201 of FIG. 2. Link 300 includes a housing 301, at least two electromagnetic coils 302, 303 and a hollow passage 304 that may be sized to allow for image transmitting cords, such as cord 305 to pass through link 300. A proximal end of cord 305 may be connected to a control system (such as control system 102 of FIG. 1) and a distal end of cord 305 may be connected to an image capturing device (such as image capturing device 105 of FIG. 1). Cord 305 may be utilized for transmitting images from the image capturing device to the control system.

Referring to FIG. 3, according to an exemplary embodiment, housing 301 may be separated into smaller housings 306, 307 that may be sized to support electromagnetic coils 302, 303 respectively therein. An electromagnetic coil, such as electromagnetic coil 302 may include a wire 308 wound around a core 309 that may be housed inside a small housing, such as housing 306. In an embodiment, wire 308 may be connected to a control system (such as control system 102 of FIG. 1) and the control system may stimulate coil 302 by sending electrical signals through wire 308.

With further reference to FIG. 3, link 300 may be connected at both sides to adjoining links by for example revolute joints (also called pin joints). To this end, according to an exemplary embodiment, link 300 may include at least two opposing extended fingers 310, 311 (or projections) that may be located at opposite sides of link 300 at a first side 312 thereof. According to an exemplary embodiment, link 300 may include two opposite recessed portions (only one recessed portion 313 is visible and labeled in FIG. 3) that may be located at opposite sides of link 300 at a second side 314 thereof. Extended fingers 310, 311 may have holes 316 thereon and the recessed portions may also have holes 317 thereon. In an embodiment, holes 316 and 317 are sized to receive pins therein.

Figure 4A:
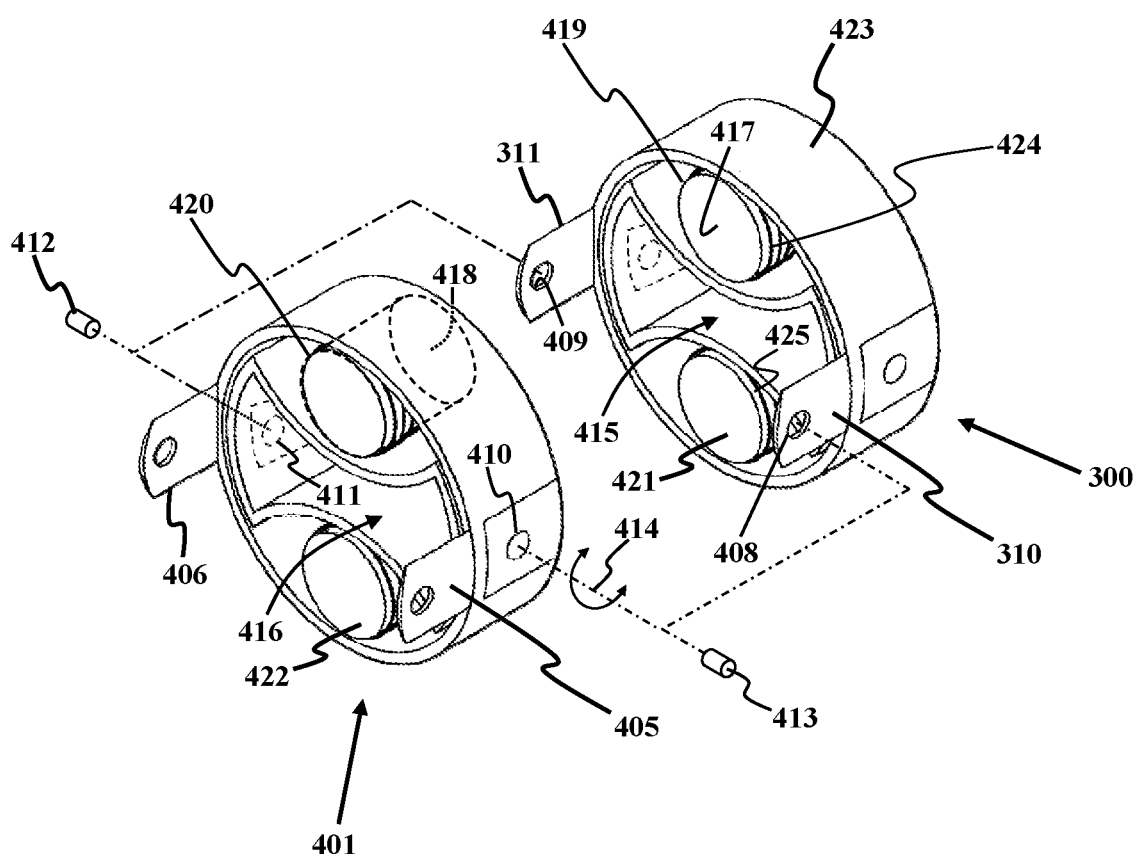
FIG. 4A shows two adjoining links in an articulating portion of an elongated probe, consistent with an exemplary embodiment of the present disclosure.
Figure 4B:
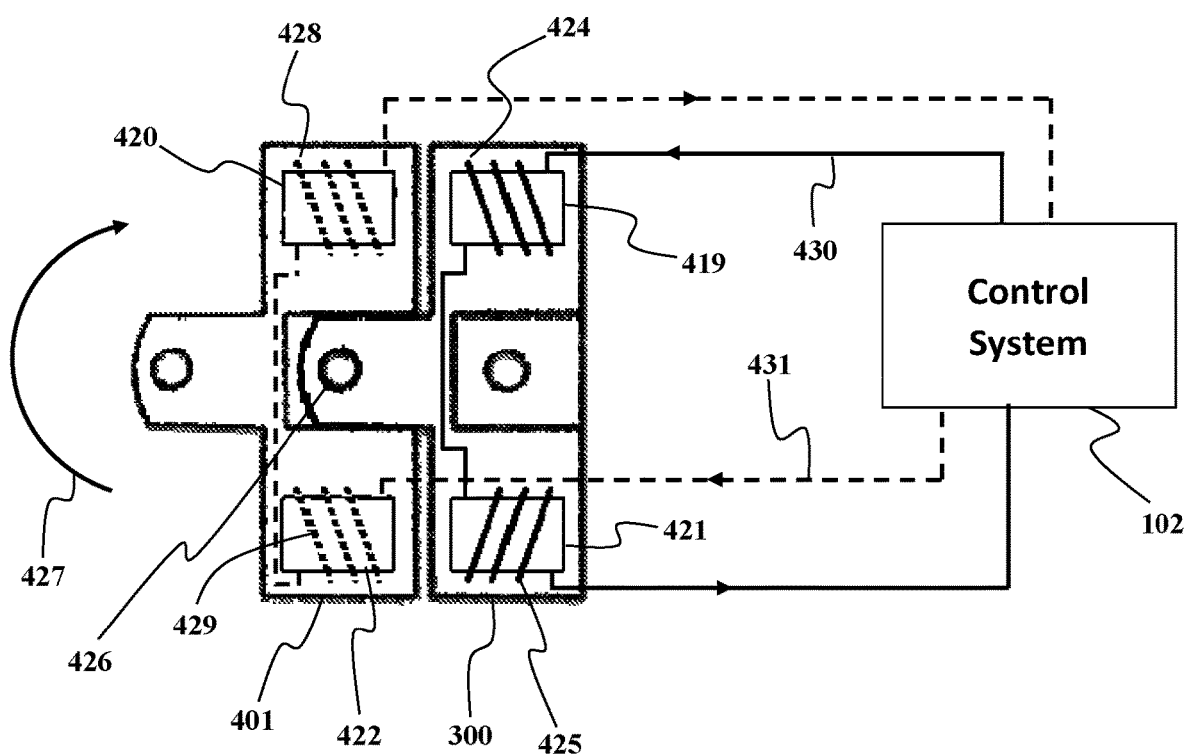
FIG. 4B is a schematic representation of the articulating portion of an elongated probe, consistent with an exemplary embodiment of the present disclosure.

FIG. 4A shows two adjoining links in an articulating portion of an elongated probe, consistent with an exemplary embodiment of the present disclosure. FIG. 4B is a schematic representation of the articulating portion of an elongated probe that includes two adjoining links shown in FIG. 4A.

Referring to FIGS. 3 and 4A, opposite extended fingers 310 and 311 of first link 300 may be coupled with recessed portions 405 and 406 of a second link 401 via revolute joints. Link 401 may be similar to link 300 or any other links 201 of FIG. 2. In an exemplary embodiment, holes 408 and 409 on the opposite extended fingers 310 and 311 of first link 300 may be aligned with holes 410 and 411 of the recessed portions on second link 401 and pins, such as pins 412 and 413 may be placed inside holes 408-411 to form opposing revolute or pin joints that allow for a relative rotational movement of first and second links 300, 401 about a single axis 414. First and the second links 300, 401 may be interconnected with a gap therebetween. This interconnection mechanism runs through the articulating portion from one link to the next and allows each link to pivot relative to its adjoining links. In another embodiment, a recessed portion of a link may carry a protruding stud and an extended finger may engage a corresponding stud from recessed portion of an interconnected link.

According to an exemplary embodiment, once the links are interconnected, the hollow passages of interconnecting links are in alignment and may carry any image transmitting cords or other substances that may transmit images. In additional embodiment, the camera may be able to transfer data to the controller or additional devices through other transmission mechanisms. Furthermore, coils of each link are placed near corresponding coils of an adjoining link, such that their end surfaces are in the proximity of one another with a gap between the end surfaces. This allows for the coils to have a suitable distance from one another in order to attract or repulse one another once voltage is applied to their windings. For further clarification, as an example, referring to FIG. 4A, once first link 300 and second link 401 are interconnected, a first hollow passage 415 of first link 300 will be aligned with a second hollow passage 416 of second link 401 to provide a hollow channel for a transmitting cord to pass through. Furthermore, end surface 417 of a first coil 419 will be in the proximity of an end surface 418 of a second coil 420.

With further reference to FIG. 4A, each link may have two electromagnetic coils disposed inside the link at opposing sides. For example, first link 300 has electromagnetic coil 419 that is disposed inside upper portion of first link 300 and electromagnetic coil 421 that is disposed inside lower portion of first link 300. Similarly, second link 401 has electromagnetic coil 420 that is disposed inside upper portion of second link 401 and electromagnetic coil 422 that is disposed inside lower portion of second link 401.

Referring to FIGS. 4A and 4B, windings 424 and 425 of first link 300 may be connected with one another and with control system 201 via wire 430, and windings 428 and 429 of second link 401 may be connected with one another and with control system 102 via wire 431, according to exemplary embodiment shown in FIG. 4B. Control system 102 may stimulate electromagnetic coils 419 and 421 of first link 300 by sending an electric signal (i.e., electric current with a first direction) through wire 430 and similarly, control system 102 may stimulate electromagnetic coils 420 and 422 of second link 401 by sending an electric signal (i.e., electric current in a first direction) through wire 431.

Referring to FIG. 4A, according to an exemplary embodiment, upper and lower windings 424 and 425 of first link 300 may be wound in opposite directions, e.g., upper winding 424 may be wound clockwise while lower winding 425 may be wound counter-clockwise or vice versa. Windings 428 and 429 of second link 401 may be wound in a same direction as upper winding 424 of first link 300.

According to an exemplary embodiment, once control system 102 sends electrical signals through wires 430 and 431 in opposite directions, regarding the winding directions described hereinabove, coils 419 and 420 will be magnetically stimulated into attracting one another, while coils 421 and 422 will be magnetically stimulated into repulsing one another. Magnetic attraction and repulsion forces urge second link 401 to pivot upward about pivot point 426 about axis 414 in a direction shown by arrow 427.

According to another exemplary embodiment, once control system 102 sends electrical signals through wires 430 and 431 in similar directions, regarding the winding directions described hereinabove, coils 419 and 420 will be magnetically stimulated into repulsing one another, while coils 421 and 422 will be magnetically stimulated into attracting one another. Magnetic attraction and repulsion forces urge second link 401 to pivot downward about pivot point 426 about axis 414 in a direction opposite to that shown by arrow 427.

Figure 5A:
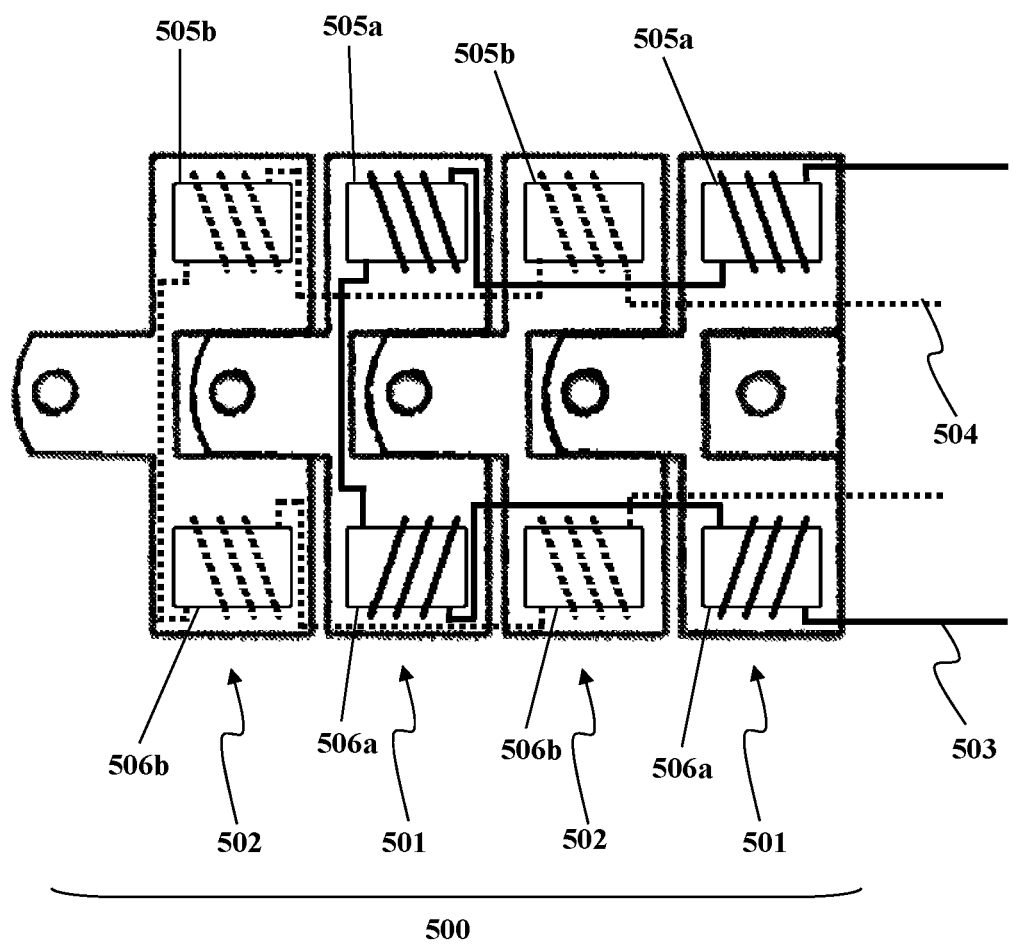
FIGS. 5A and 5B are schematic representation of a first articulating segment of a video probe, consistent with one exemplary embodiment of the present disclosure.

FIG. 5A is a schematic representation of a first articulating segment 500 of a video probe, consistent with one exemplary embodiment of the present disclosure. First articulating segment 500 may include a series of interconnected links 501 and 502. Every other link in first articulating segment 500 may have similar electromagnetic coil arrangements, for example links 501 may be similar to first link 300 (labeled in FIGS. 3, 4A and 4B) and links 502 may be similar to second link 401 (labeled in FIGS. 3, 4A and 4B). Upper coils 505a and 505b may have similar windings wound in similar directions and from lower coils, coils 506a and 506b may have windings wound in opposite directions. Coils 505a and 506a may be connected to one another and to the control system 102 (labeled in FIGS. 1 and 4B) via wire 503. While, Coils 505b and 506b may be connected to one another and to the control system 102 (labeled in FIGS. 1 and 4B) via wire 504.

Figure 5B:
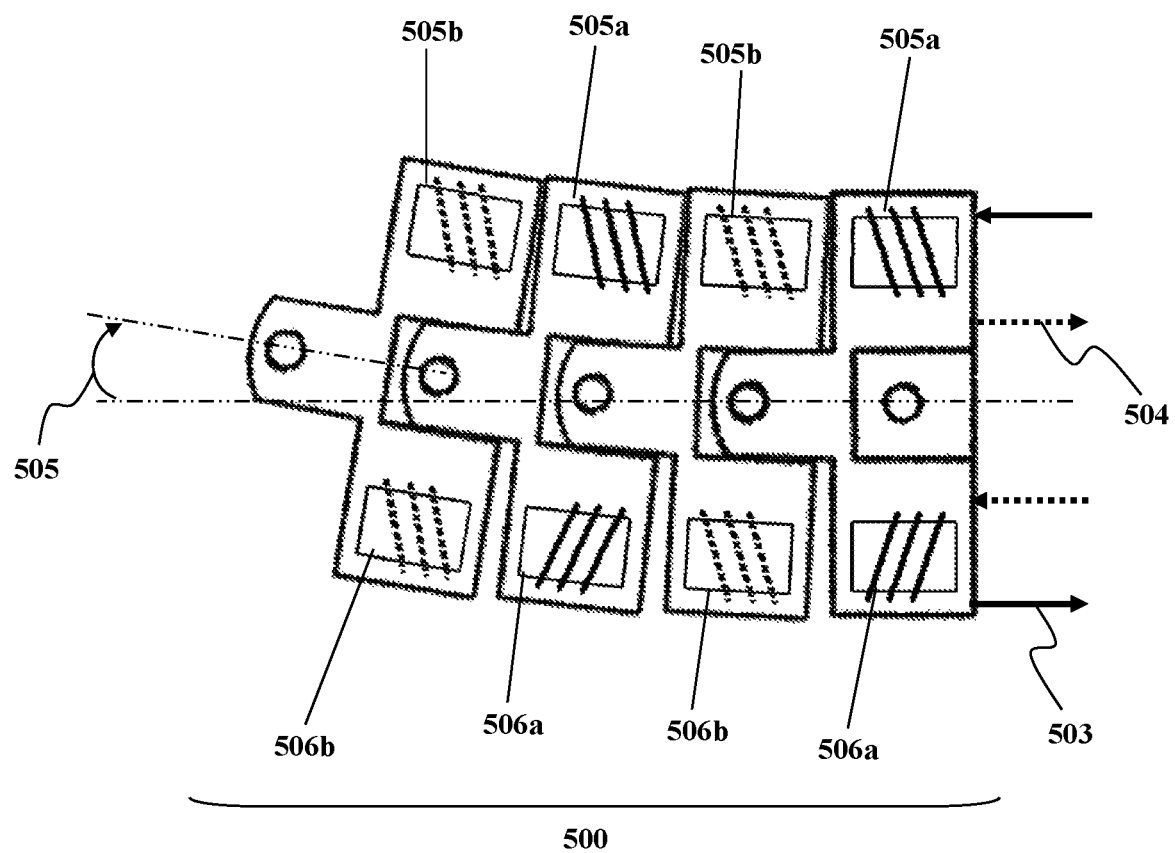

Referring to FIG. 5B, according to an exemplary embodiment, once the control system 102 sends electrical signals through wires 504 and 503 in opposite directions, upper coils 505a and 505b attract one another and lower coils 506a and 506b repulse one another and force first articulating portion 500 to curve upward in a direction shown by arrow 505. With further reference to FIG. 5B, according to another exemplary embodiment, once the control system 102 sends electrical signals through wires 504 and 503 in similar directions, upper coils 505a and 505b repulse one another and lower coils 506a and 506b attract one another and force first articulating segment 500 to curve downward in a direction opposite to that shown by arrow 505.

Figure 5C:
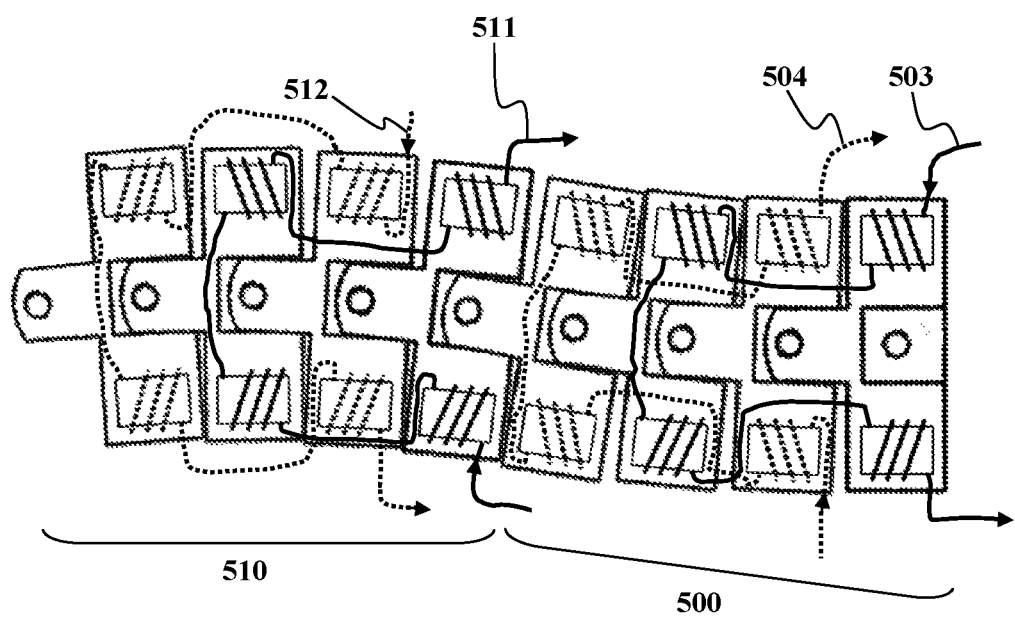
FIG. 5C is a schematic representation of two articulating segments of a video probe, consistent with one exemplary embodiment of the present disclosure.

FIG. 5C is a schematic representation of an articulating portion of an elongated video probe, consistent with an exemplary embodiment of the present disclosure. Referring to FIG. 5C, the articulating portion may include at least two articulating segments 500 and 510. Articulating segment 510 may be joined with an adjoining articulating segment by a relative 180° offset rotation from articulating segment 500 to articulating segment 510, as shown in FIG. 5C. According to other exemplary embodiments, the articulating portion may include a number of articulating segments, similar to articulating segments 500 and 510, where each articulating segment is joined with an adjoining articulating segment by a relative 180° offset rotation from one articulating segment to the next.

With further reference to FIG. 5C, each articulating segment can be separately connected with a control system (not shown in FIG. 5C). For example, articulating segment 500 may be connected with the control system via wires 503 and 504, while articulating segment 510 may be connected with the control system via wires 511 and 512. The control system may be configured to send separate electrical signals through wires of each articulating segment. For example, if the control system sends electrical signals with opposite directions through wires 503 and 504, the articulating segment 500 curves upward as shown in FIG. 5C, and if the control system sends electrical signals with opposite directions through wires 511 and 512, the articulating segment 500 curves downward as shown in FIG. 5C. This may allow for curving the first articulating segment 500 and the second articulating segment 510 in similar directions or alternatively in opposite directions.

Figure 6:
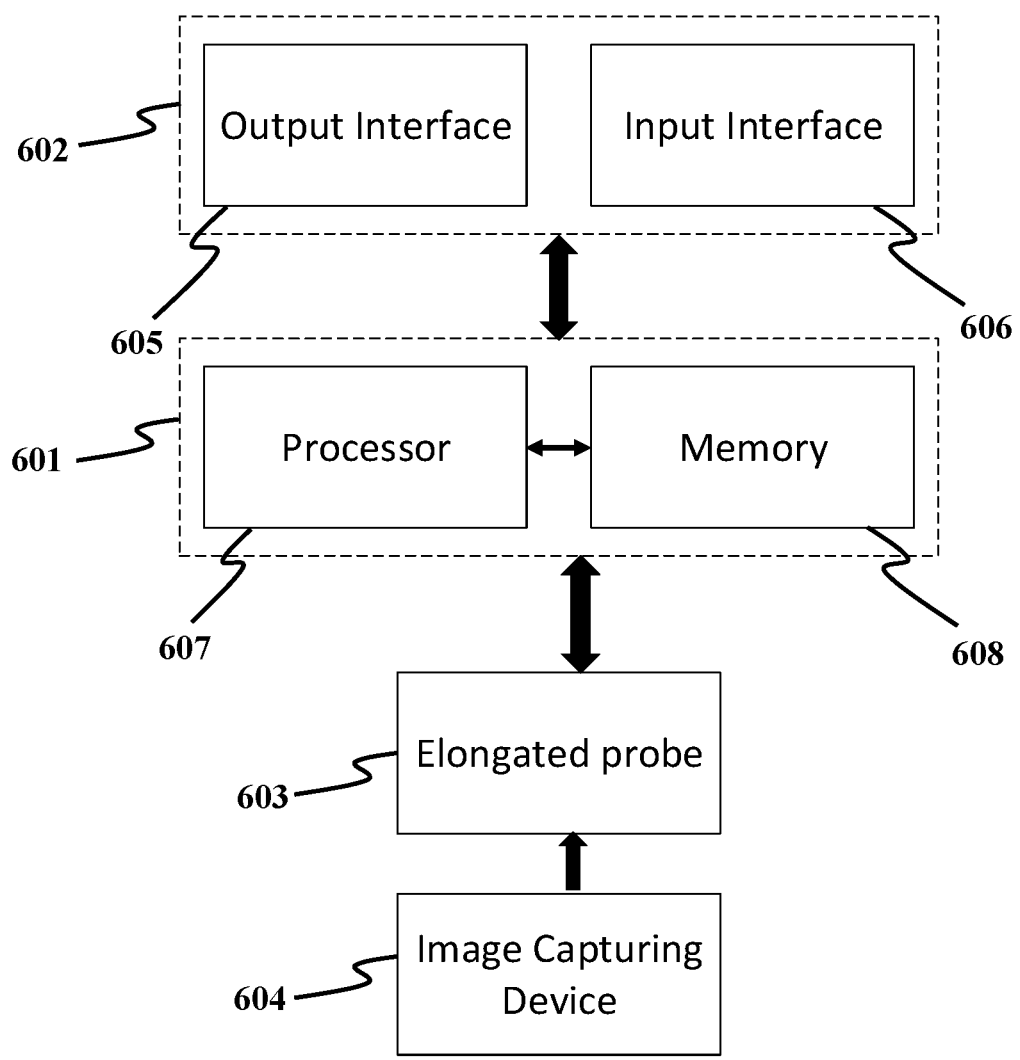
FIG. 6 is a schematic functional block diagram of a video probe system, according to an exemplary embodiment of the present disclosure.

FIG. 6 is a schematic functional block diagram of a video probe system 600, according to an exemplary embodiment of the present disclosure. With reference to FIG. 6, an embodiment of the present disclosure is described with the aid of functional building blocks illustrating the implementation of specified functions. Video probe system 600 may be implemented as a video probe apparatus, such as video probe apparatus 100 of FIG. 1.

Referring to FIG. 6, video probe system 600 may include a control system 601, a user interface unit 602, an elongated probe 603, and optionally an image capturing device 604 attached to elongated probe 603. Elongated probe 603 may be utilized, as was described in detail in preceding sections of this disclosure, to navigate image capturing device 604 in an area of interest.

Control system 601 may be similar to control system 102 of FIG. 1. According to an implementation, control system 601 may be coupled to elongated probe 603, user interface unit 602, and image capturing device 604 through, for example, wired links (not explicitly visible in FIG. 6), wireless links (not explicitly visible in FIG. 6), or a combination of wired and wireless links. Control system 601 may be configured to control orientation and motions of elongated probe 603 by sending electric signals to elongated probe 603 and control system 601 may also be configured to control image capturing device 604.

User interface unit 602 may be configured to receive data input from a user. According to an exemplary embodiment, user interface unit 602 may include an output interface 605, such as a graphical user interface unit (GUI) 108 (labeled in FIG. 1) and an input interface 606, such as control levers and buttons 109 (labeled in FIG. 1). User interface unit 602, in combination with control system 601, may allow a user to interactively control the orientation of image capturing device 604 via controlling the rotational movements of articulating portion of elongated probe 603. Data input by the user may include, for example, a desirable orientation for image capturing device 604 or commands regarding capture of an image or video from inside the area of interest.

Control system 601 may be operatively coupled to user interface unit 602, for purposes that may include calculating electrical signals that must be sent to elongated probe 603. The calculation of the electrical signals may be based, at least in part, on data received from a user through user interface unit 602. Control system 601 may include a processor 607 and a memory 608 for including executable instructions that, when executed by processor 607 cause control system 601 to perform operations to further processes and methods disclosed herein. Such operations may include, for example, conversion of desirable orientation of image capturing device 604 that is received from user interface unit 602, to appropriate units of electrical signals that must be sent to elongated probe 603 in order to change the orientation of image capturing device 604.

EXAMPLE

Figure 7:
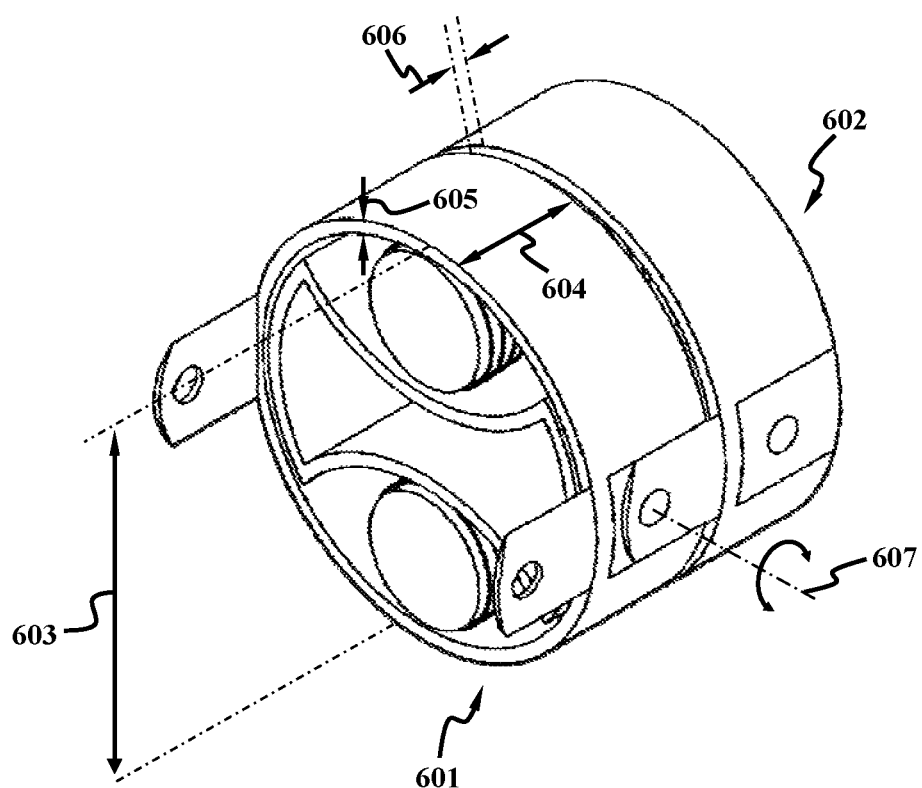
FIG. 7 illustrates an exemplary embodiment of two adjoining links in an articulating portion, consistent with an exemplary embodiment of the present disclosure.

In this example, an exemplary embodiment of links of an articulating portion of an elongated probe is disclosed. This exemplary embodiment, as described herein may be suitable for video-scopes and borescopes. FIG. 7 illustrates an exemplary embodiment of two adjoining links 701 and 702 in the articulating portion. Link 701 has a diameter 703 of 6 mm, a width 704 of 2 mm, and a thickness 705 of 0.5 mm. All links, including link 702 have similar dimensions as that of link 701. There is a gap 706 of 0.2 mm between links 701 and 702. These dimensions allow for a rotational movement of ±3.8° of each link about its respective rotation axis 707. In this example, the articulating portion has 16 interconnected links, which allows for a ±60° rotation of the articulating portion.

While the foregoing has described what are considered to be exemplary embodiments, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments. This is for purposes of streamlining the disclosure, and is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

While various embodiments have been described, the description is intended to be exemplary, rather than limiting and it will be apparent to those of ordinary skill in the art that many more embodiments and embodiments are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:

1. A video probe, comprising:
    an elongated probe including an articulating portion, the articulating portion comprising at least two interconnected links, wherein:
        each respective link is connected to an adjoining link by a single-axis joint, wherein each respective link pivots relative to the adjoining link about an axis of the single-axis joint,
        each respective link includes a first electromagnetic coil disposed within the link at a first side thereof and a second electromagnetic coil at a second side thereof; and
    a controller coupled with the first electromagnetic coil and the second electromagnetic coil of each respective link, the controller configured to stimulate the first electromagnetic coil to attract a corresponding first electromagnetic coil of an adjoining link and the second electromagnetic coil to repulse a corresponding second electromagnetic coil of an adjoining link thereby causing the link to pivot about the axis of the single-axis joint.

2. The video probe according to claim 1, wherein the controller is coupled with the first electromagnetic coil of each respective link via electrical wiring extending from the controller through the elongated probe and coupled with the first electromagnetic coil in a first winding direction.

3. The video probe according to claim 2, wherein the controller is configured to send electrical signals to the first electromagnetic coil through the electrical wiring to stimulate the first electromagnetic coil of each link to attract a corresponding first electromagnetic coil of an adjoining link.

4. The video probe according to claim 2, wherein the controller is coupled with the second electromagnetic coil of each link via electrical wiring extending from the controller through the elongated probe and coupled with the second electromagnetic coil in a second winding direction.

5. The video probe according to claim 4, wherein the controller is configured to send electrical signals to the second electromagnetic coil through the electrical wiring to stimulate the second electromagnetic coil of each link to attract a corresponding first second electromagnetic coil of an adjoining link.

6. A video probe, comprising:
    an elongated probe including an articulating portion, the articulating portion comprising at least a first articulating segment and a second articulating segment, wherein:
    each articulating segment comprises at least two interconnected links, wherein each link connected to an adjoining link by a single-axis joint, wherein each link pivots relative to the adjoining link about an axis of the single-axis joint, wherein each link includes a first electromagnetic coil disposed within the link at a first side thereof, and a second electromagnetic coil at a second side thereof, wherein, each segment is joined with an adjoining segment by a relative 180° offset rotation from one articulating segment to the next; and
    a controller functionally coupled with the elongated probe, configured to magnetically stimulate the interconnected links of the first articulating segment thereby causing the first electromagnetic coil to attract a corresponding first electromagnetic coil of an adjoining link and the second electromagnetic coil to repulse a corresponding second electromagnetic coil of an adjoining link, the controller further configured to magnetically stimulate the interconnected links of the second articulating segment thereby causing the first electromagnetic coil to attract a corresponding first electromagnetic coil of an adjoining link and the second electromagnetic coil to repulse a corresponding second electromagnetic coil of an adjoining link.

* * * * *